(12) United States Patent
Osso et al.

(10) Patent No.: US 8,889,897 B2
(45) Date of Patent: Nov. 18, 2014

(54) ELECTROCARBOXYLATION SYNTHESIS FOR OBTAINING INTERMEDIATES USEFUL FOR THE SYNTHESIS OF SPAN DERIVATIVES

(71) Applicant: Air Products and Chemicals, Inc., Allentown, PA (US)

(72) Inventors: J Oriol Osso, Barcelona (ES); Lourdes F. Vega, Barcelona (ES); Illuminado Gallardo, Bellaterra (ES); Gonzalo Guirado, Bellaterra (ES); Ana Belen Gomez, Bellaterra (ES); Francisca Irene Reche, Bellaterra (ES)

(73) Assignee: Air Products and Chemicals, Inc., Allentown, PA (US)

( * ) Notice: Subject to any disclaimer, the term of this patent is extended or adjusted under 35 U.S.C. 154(b) by 0 days.

(21) Appl. No.: 13/706,732

(22) Filed: Dec. 6, 2012

(65) Prior Publication Data
US 2013/0165684 A1    Jun. 27, 2013

(30) Foreign Application Priority Data
Dec. 23, 2011    (EP) .................................... 11382396

(51) Int. Cl.
| | | |
|---|---|---|
| *C07C 255/30* | (2006.01) | |
| *C07C 255/47* | (2006.01) | |
| *C25B 3/00* | (2006.01) | |

(52) U.S. Cl.
CPC ............... *C25B 3/00* (2013.01); *C07C 2103/24* (2013.01); *C07C 255/47* (2013.01)
USPC .......................................... 558/357; 548/411

(58) Field of Classification Search
None
See application file for complete search history.

(56) References Cited

U.S. PATENT DOCUMENTS

| | | |
|---|---|---|
| 4,072,583 A | 2/1978 | Hallcher et al. |
| 4,708,780 A | 11/1987 | Silvestri et al. |
| 5,089,661 A | 2/1992 | Maspero et al. |
| 6,342,149 B1 | 1/2002 | Koster et al. |
| 6,806,283 B2 | 10/2004 | Glennon et al. |

FOREIGN PATENT DOCUMENTS

| | | |
|---|---|---|
| EP | 0 028 430 A1 | 5/1981 |
| WO | 99/45173 A1 | 9/1999 |
| WO | 2004/111309 A2 | 12/2004 |

OTHER PUBLICATIONS

Database Registry, Chemical Abstracts Service, Columbus, Ohio, US; Feb. 3, 1988, XP002672392, Database accession No. 200633-65-4.

Rio G et al, "Reactions de Substitution, D'Addition 1,6 et D'Alcoylation Chez Des Cyano-9 Anthracenes Substitutes," Bulletin De La Societe Chimique de France, Societe Franciase De Chimie, Paris, France, Jan. 1, 1961, XP-001181070, pp. 831-836.

M. Martynoff, No 50, Note de laboratoire. Action des organomagnesiens mixtes sur le-cyano-9-anthracene. Cyano-9 cyclohexyl-10 dihydro-9,10-anthracene et cyano-9 benzyl -10 dihydro-9,10 anthracene, Bulletin De La Societe Chimique De France, 1962, XP002672393, p. 272.

*Primary Examiner* — Nyeemah A Grazier
(74) *Attorney, Agent, or Firm* — Michael K. Boyer

(57) ABSTRACT

The present invention relates to a process for obtaining a compound of formula (1), (2) or (3) by means of a electrocarboxylation with $CO_2$. The present invention also relates to the new intermediates (1) and (2). The present invention further relates to the use of intermediates (1) and (2) as starting materials for the synthesis of SPAN derivatives.

10 Claims, No Drawings

ELECTROCARBOXYLATION SYNTHESIS FOR OBTAINING INTERMEDIATES USEFUL FOR THE SYNTHESIS OF SPAN DERIVATIVES

BACKGROUND OF THE INVENTION

The present invention relates to the field of electrochemical carboxylation synthesis.

Serotonin is a biochemical messenger and regulator, synthesized from the essential amino acid L-tryptophan. In humans it is found primarily in the central nervous system, gastrointestinal tract, and blood platelets. Serotonin mediates several important physiological functions including neurotransmission, gastrointestinal motility, hemostasis, and cardiovascular integrity.

Serotonin receptors are cell-surface proteins that bind serotonin and trigger intracellular changes which influence the behaviour of cells. Several types of serotonin receptors have been recognized which differ in their pharmacology, molecular biology, and mode of action.

It is been disclosed that compounds like spiro-[9,10-dihydroanthracene]-9,3'-pyrrolidine (SPAN) and derivatives thereof are selective serotonin receptor antagonist (5-HT). By antagonist of serotonin receptors is meant compounds that block the action of endogenous serotonin at the receptor and prevent its activation. These compounds are useful as antidepressant and anti-anxiety agents and are of pharmacological interest.

There are several known serotonin receptors and types of antagonists currently used.

For example, serotonin 5-HT1 receptors are in the central nervous system. An excess of serotonin availability at the serotonin 1 A receptor causes serotonin syndrome. Agonists of serotonin 5-HT1 D, such as sumatriptan, are used to treat migraine headaches.

As for serotonin 5-HT2 receptors, antagonists, such as risperidone, are used to treat schizophrenia. Their agonists, such as fluoxetine, are used to treat depression. Agonists of the 5-HT2C receptor, such as lorcaserin, decreases appetite via the proopiomelanocortin system. However, non-selective activation of the 5-HT2B receptors as well as the 5-HT2C receptors by fenfluramine and dexfenfluramine may damage heart valves via agonism of 5-HT2B receptors on valvular cells.

As for serotonin 5-HT3 receptors, they stimulate gastrointestinal motility. Antagonists, such as ondansetron, are used as an antiemetic for chemotherapy. Antagonists, such as alosetron, are to treat diarrhea-predominant irritable bowel syndrome.

U.S. Pat. No. 6,806,283 (Glennon et al.) discloses the use of SPAN as selective serotonin receptor antagonists and methods of their use as anti-depressant and anti-anxiety agents. Different synthesis routes for obtaining of SPAN and other derivatives are also disclosed, although none of electrochemical type.

Due to the importance of these compounds as anti-depressant and anti-anxiety agents it would be of great help to have alternative advantageous routes for obtaining said compounds.

The present inventors have surprisingly found an alternative synthesis route for obtaining SPAN and derivatives thereof by applying a step of controlled potential electrolysis on the starting material under $CO_2$ atmosphere. Advantageously, as a result of this step new intermediates have also been found.

Electrochemical carboxylation is a chemical reaction already used in the synthesis of chemical compounds.

Thus, U.S. Pat. No. 5,089,661 discloses the synthesis of a 2-aryl-propionic acids having anti-inflammatory properties using electrocarboxylation for the synthesis of the starting salt. U.S. Pat. No. 4,072,583 reports on the electrolytic carboxylation of carbon acids via electrogenerated bases leading to carboxylated carbon acids. Also U.S. Pat. No. 4,708,780 discloses a process for electrocarboxylating carbonyl compounds from $CO_2$ for the production of α-hydroxycarboxylic acids.

The disclosure of the previously identified patents is hereby incorporated by reference.

In view of the prior art, there is still the need for finding new advantageous routes for obtaining SPAN and derivatives thereof. None of the previous documents discloses or suggests a synthesis route based on electrochemical carboxylation for obtaining new or not new intermediates which in turn are useful for obtaining SPAN and derivatives thereof.

BRIEF SUMMARY OF THE INVENTION

The present invention relates to a process for obtaining a compound selected from the group consisting of

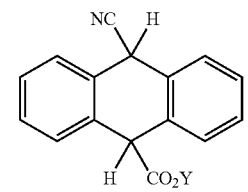

(1)

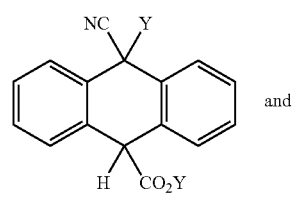

and (2)

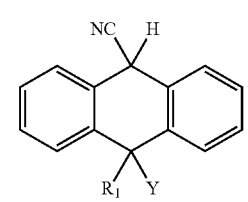

$R_1$ = H or $CH_3$ (3)

wherein Y is alkyl or benzyl group,
by means of a electrocarboxylation with $CO_2$. These compounds are intermediates in the synthesis of SPAN and derivatives thereof which can be isolated, purified and characterized.

The present invention also relates to the new intermediates (1) and (2).

The present invention further relates to the use of intermediates (1) and (2) as starting materials for the synthesis of SPAN derivatives.

DETAILED DESCRIPTION OF THE INVENTION

In a first aspect, the present invention relates to a process for obtaining a compound selected from the group consisting of

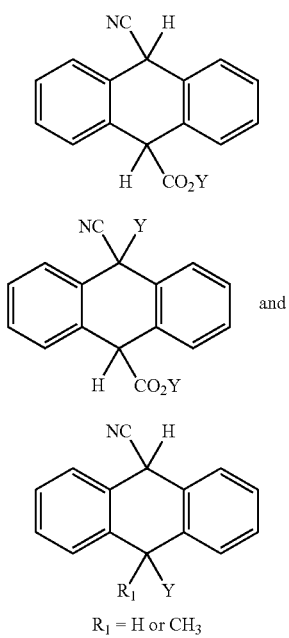

$R_1$ = H or $CH_3$ wherein Y is alkyl or benzyl group,
comprising the steps of:
a) reacting a solution of compound

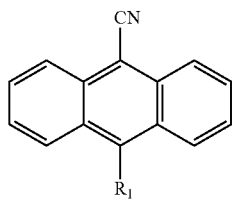

wherein $R_1$ is H or methyl;
with a saturated solution of $CO_2$ under a potential between —1.5 V and −2.0V;
b) adding an alkylating agent YX, wherein Y is alkyl or benzyl group and X is I, Br or Cl, preferably YX being alkyl iodide or bromide, in a concentration in 2 to 50 fold molar excess;
c) bubbling the resultant solution under inert gas, preferably $N_2$.

The reaction was performed in a standard electrochemical cell at room temperature being the time of the reaction between 2-4 h.

The working electrodes for the process are usually carbon graphite or silver.

In a preferred embodiment of step (a), the solution of the compound is formed with organic aprotic solvents and electrolyte salts.

In a more preferred embodiment said solvent is DMF (dimethylformamide), ACN (acetonitrile), DMS (dimethylsulfoxide), or mixtures thereof.

In a more preferred embodiment, said electrolyte salt is a tetralkylammonium salt, preferably said tetralkylammonium salt is $TEABF_4$. Preferably, the concentration of said electrolyte salt is about 0.1 M.

In another preferred embodiment, said potential applied lies between −1.7 and −2 V.

In another preferred embodiment, the concentration of the compound in step a) is between 10 and 100 mM.

In another preferred embodiment for step (b) the fold molar excess of the concentration for the alkylating agent in step (b) is between 4 and 50.

It is noted that any of the preferred embodiments disclosed herein can be combined with one or more of the remained preferred embodiments encompassed herein.

In this process according to the first aspect of the invention, the activation of $CO_2$ reactivity leads to useful yields of carboxylic compounds (20-60%). The reaction is selective and clean, leading to one carboxylic compound and recovering the unreacted material for being recycled. In addition, said process using an electrochemical reaction is environmentally friendly, provides good yields and the starting reactants (10-substituted-9-cyanoanthracene) and $CO_2$ are easily available and cheap reagents. Furthermore, $CO_2$ is used as a building block for SPAN synthesis, which gives an added value to $CO_2$ and provides industrial uses which can be applied to valorise the large amount of $CO_2$ that can be captured from different sources.

The compounds obtained from the process according to the first aspect of the invention were purified using either column chromatography or semi-preparative thin layer chromatography depending on the quantity of the product.

In a second aspect, the present invention relates to the new intermediate of formula (1):

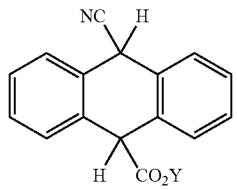

wherein Y is as defined above.

In this second aspect, the present invention also relates to the new intermediate of formula (2):

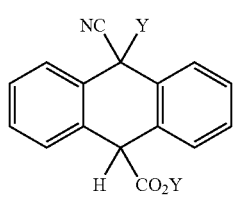

wherein Y is as defined above.

In a third aspect, the present invention also relates to the use of compounds of formula (1) or (2) as starting materials for the synthesis of SPAN derivatives. Preferably, starting from compound (1) a SPAN derivative like alkyl-10-cyano-9,10-dihydro-9-anthracenecarboxylate can be produced; similarly, from compound (2) a SPAN derivative like alkyl-10-cyano-10-methyl-9-hydro-9-anthracenecarboxylate can be produced. Also disclosed herein is the use of (3) as a starting material for obtaining a SPAN derivative like 9-cyano-10-alkyl-10-methyl-9-hydroanthracene or 9-cyano-10-alkyl-9,10-dihydroanthracene.

Said synthesis starting with compounds of formula (1) and (2) can be carried out by any conventional synthetic route.

The following Examples are offered for illustrative purposes only and are not intended to limit the scope of the present invention in any way

EXAMPLES

Example 1

The synthesis of 10-cyano-9,10-dihydro-9-anthracenecarboxylate methyl (1) was carried out as depicted in Scheme 1

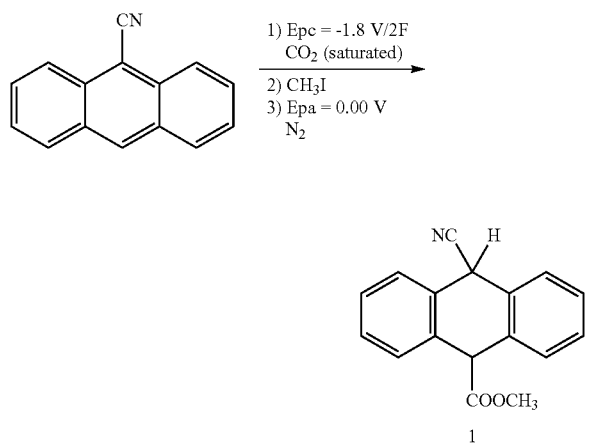

The controlled potential electrolysis was carried out in DMF-TEABF$_4$ (10 ml, 0.1 mol/l) containing 10 mM of 9-Cyanoanthracene in an undivided glass cell. Carbon dioxide was allowed to flow during the electrolysis process. The solution was electrolyzed over a carbon graphite rod or silver sheet working electrode and platinum counter electrode. The solution was exposed to potential of −1.8 V vs SCE to pass a total charge corresponding to 2F. At the end of the electrolysis, methyl iodide (alkylating agent) was added in 2-fold molar excess, and the solution was oxidized at 0.0 V vs. SCE and left under constant bubbling of N$_2$ for 45 minutes.

Diethyl ether (10 ml) was added to crude solution, then that solution was washed with 1 mol/l of HCl (3×10 ml). The organic phase was washed with water (2×10 ml). The aqueous layers were washed with diethyl ether (30 ml) and neutralized with water (2×30 ml). The organic layers were dried over anhydrous Na$_2$SO$_4$ and evaporated under reduced pressure to give a yellow solid. The product was purified by thin layer chromatography using dichloromethane: n-hexane (6:4) as eluent to give 0.0115 g of pure (1) (12%) as a yellow solid. GC-MS (70 eV): m/z (%) 263.1 (10) [M$^+$], 204.1 (100) [M$^+$-C$_2$H$_3$O$_2$], 176.1 (17), 151.1 (6), 88.1 (6). The instruments used for GC or GC-MS analysis were a standard instrument from Perkin Elmer with an Elite-5 column.

Example 2

The synthesis of 10-cyano-10-methyl-9-hydro-9-anthracenecarboxylate methyl (2) was carried out as depicted in Scheme 2

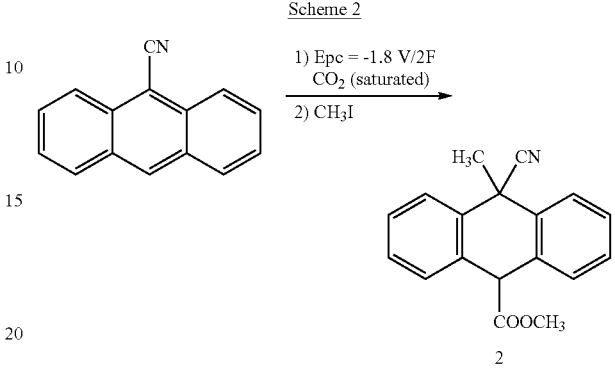

The controlled potential electrolysis was carried out in DMF-TEABF$_4$ (10-250 ml, 0.1 mol/l) containing 10 mM of 9-Cyanoanthracene in an undivided glass cell. Carbon dioxide was allowed to flow during the electrolysis process. The solution was electrolyzed over a carbon graphite rod or silver sheet working electrode and platinum counter electrode. The solution was exposed to potential of −1.8 V vs SCE to pass a total charge corresponding to 2F. At the end of the electrolysis, methyl iodide (alkylating agent) was added in 4-fold molar excess, and the solution was left under constant bubbling of N$_2$ for 45 minutes.

Diethyl ether (10 ml) was added to crude solution, then that solution was washed with 1 mol/l of HCl (3×10 ml). The organic phase was washed with water (2×10 ml). The aqueous layers were washed with diethyl ether (30 ml) and neutralized with water (2×30 ml). The organic layers were dried over anhydrous Na$_2$SO$_4$ and evaporated under reduced pressure to give a yellow solid. The product was purified by thin layer chromatography using dichloromethane: n-hexane (6:4) as eluent to give 0.0115 g of pure (2) (70%) as yellow crystals. GC-MS (70 eV): m/z (%) 277.1 (8) [M$^+$], 218.2 (100) [M$^+$-C$_2$H$_3$O$_2$], 203.2 (100) [M$^+$-C$_3$H$_6$O$_2$], 191.2 (10), 176.1 (10); $^1$H NMR (250 mHz, CDCl$_3$) δ (ppm): 2.00 (s, 3H), 3.66 (s, 3H), 5.14 (s, 1H), 7.42 (m, 6H), 7.86 (d, J=7.81 Hz, 2H). The instruments used for GC or GC-MS analyses were a standard instrument from Perkin Elmer with an Elite-5 column.

Comparative Example with Prior Art

The chemical synthesis disclosed in prior art for obtaining intermediates similar to those disclosed herein involves at least two chemical steps with a 60 and 70% yield of each step, respectively (see below).

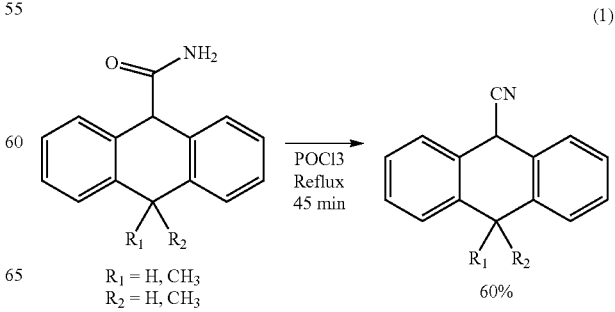

-continued (2)

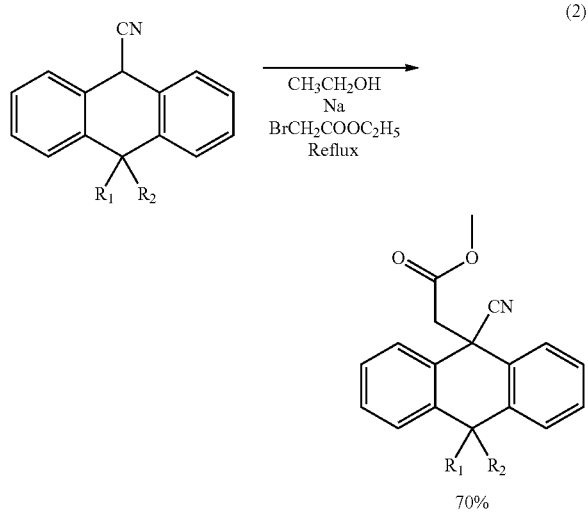

70%

In the present invention, by using an electrochemical carboxylation step with $CO_2$ we can achieve more than a 70% of the desired product in one step and recovering the 30% of the non-reactive material (which is the initial reactant). The unreacted starting material can be recycled at the end of the process.

The invention claimed is:

1. Process for obtaining a compound selected from the group consisting of formula (1)

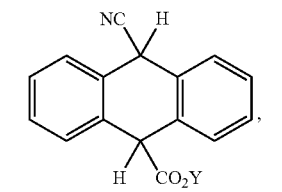

formula (2)

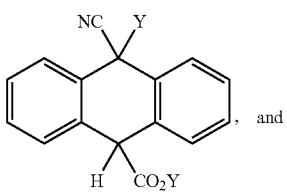
, and formula (3)

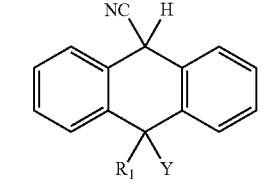

$R_1$ = H or $CH_3$ wherein Y is alkyl or benzyl group, comprising the steps of:
a) reacting a solution of compound

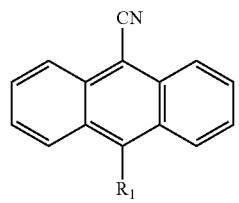

wherein $R_1$ is H or methyl;
with a saturated solution of $CO_2$ under a potential between −1.5 V and −2.0V;
b) adding an alkylating agent YX, wherein Y is alkyl or benzyl group and X is I, Br or Cl, in a concentration in 2 to 50 fold molar excess; and
c) bubbling the resultant solution under inert gas.

2. Process according to claim 1, wherein the solution of the compound in step a) is formed with organic aprotic solvents and electrolyte salts.

3. Process according to claim 2 wherein said solvent is dimethylformamide, acetonitrile, dimethylsulfoxide or mixtures thereof.

4. Process according to claim 2, wherein said electrolyte salt is a tetralkylammonium salt.

5. Process according to claim 4, wherein said tetralkylammonium salt is tetraethyl ammonium tetrafluoroborate.

6. Process according to claim 1, wherein the fold molar excess of the concentration for the alkylating agent is between 4 and 50.

7. Process according to claim 1, wherein said potential applied lies between −1.7 and −2 V.

8. Process according to claim 1, wherein the concentration of the compound in step a) is between 10 and 100 mM.

9. Process according to claim 1 wherein the compound of formula (1) is obtained:

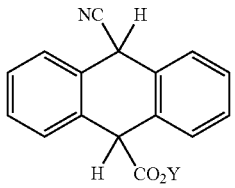

wherein Y is alkyl or benzyl group.

10. Process according to claim 1 wherein the compound of formula (2) is obtained:

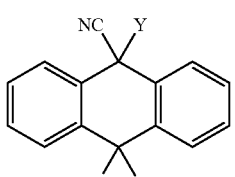

wherein Y is alkyl or benzyl group.

* * * * *